US006234173B1

(12) United States Patent
Hajianpour

(10) Patent No.: US 6,234,173 B1
(45) Date of Patent: May 22, 2001

(54) FOOT RESTRAINT APPARATUS FOR HOLDING A LEG IN PLACE DURING KNEE SURGERY

(76) Inventor: Mohammed Ali Hajianpour, 1706 Vestal Dr., Coral Springs, FL (US) 33071

(*) Notice: Subject to any disclaimer, the term of this patent is extended or adjusted under 35 U.S.C. 154(b) by 0 days.

(21) Appl. No.: 09/406,902

(22) Filed: Sep. 28, 1999

(51) Int. Cl.[7] ..................... A61B 19/00
(52) U.S. Cl. ..................... 128/869; 128/882
(58) Field of Search ..................... 128/869, 882; 602/5, 23, 26

(56) References Cited

U.S. PATENT DOCUMENTS

| | | | | |
|---|---|---|---|---|
| 3,753,557 | | 8/1973 | Kelley | 269/328 |
| 3,802,692 | | 4/1974 | Lipson | 269/325 |
| 4,091,808 | | 5/1978 | Nelson | 128/133 |
| 4,181,297 | | 1/1980 | Nichols | 269/328 |
| 4,209,012 | | 6/1980 | Smucker | 128/133 |
| 4,232,681 | * | 11/1980 | Tulaszewski | 128/882 |
| 4,299,213 | * | 11/1981 | Violet | 128/882 |
| 4,323,080 | * | 4/1982 | Melhart | 128/882 |
| 4,373,709 | * | 2/1983 | Whitt | 128/882 |
| 4,407,277 | | 10/1983 | Ellison | 128/82 |
| 4,457,302 | | 7/1984 | Caspari et al. | 128/133 |
| 4,549,540 | | 10/1985 | Caspari et al. | 128/133 |
| 5,007,912 | | 4/1991 | Albrektsson et al. | 606/87 |
| 5,514,143 | | 5/1996 | Bonutti et al. | 606/86 |

* cited by examiner

*Primary Examiner*—Michael A. Brown
(74) *Attorney, Agent, or Firm*—Ronald V. Davidge

(57) ABSTRACT

A patient's leg is clamped into place for knee surgery by placement of the lower leg and foot in a leg receiving structure which is removably attached to a platform through the use of VELCRO closures. The platform is adjustably connected to a rail of an operating table. The leg receiving structure includes a foot holder, into which the foot is strapped, and a leg holder, into which a lower part of the leg is strapped. The leg holder is pivotally mounted on the foot holder, so that the foot may be flexed as the foot holder is moved among various positions on the platform.

11 Claims, 1 Drawing Sheet

FOOT RESTRAINT APPARATUS FOR HOLDING A LEG IN PLACE DURING KNEE SURGERY

BACKGROUND INFORMATION

1. Field of Invention

This invention relates to apparatus for holding a patient's leg in place during a knee operation, and, more particularly, to apparatus for adjustably holding a foot in place relative to an operating table rail during the installation of a knee joint prosthesis.

2. Description of the Related Art

Before the development of various methods and devices for holding the lower leg and knee during knee surgery, a nurse or assistant typically held the leg in place during an operation. Since such operations were often quite lengthy, the position of the knee was often allowed to vary according to the fatigue of the nurse. Furthermore, the presence of an individual holding the leg and knee often prevented the surgeon from being able to view the operation at a desirable angle and from being able to position himself for best advantage. To overcome these disadvantages, a number of methods and devices for holding the lower leg and knee during knee surgery have been developed.

During prosthetic knee replacement surgery, it is desirable to be able to move the knee to different positions in which it is reliably held still. For example, a prosthesis may be installed with the knee flexed, and subsequently checked in one or more positions with the knee extended, and with adjustments being made as necessary.

Conventional methods for holding the knee of a patient in place on an operating table during knee surgery interpose a wedge-shaped structure below the knee. While this method rigidly holds the knee in place, the subsequent movement of the foot to adjust the position of the knee is precluded as long as the wedge-shaped structure is present to interfere with straightening the leg to lower the knee.

The patent art includes a number of descriptions of devices developed to hold the knee and lower leg during knee surgery. For example, U.S. Pat. No. 3,753,557 describes a device, including a base, adapted to be adjustably and removably secured on a horizontally disposed operating table. An upwardly inclined support supports the leg bent at an angle, preferably less than 45 degrees at the knee, with the knee elevated and with both the upper and lower legs in a substantially vertical plane, being free from obstruction to clear visible and to access to the lateral sides of the knee. The leg is also free from obstruction to lateral movement. The support is also adjustable as to the angle at which the leg may be bent and supported, and to a position in which the leg is supported with the foot elevated to an operating level for foot and ankle surgery. While this device is adjustable to vary the angle at which the leg is bent during surgery, this is variation occurs between the initial angle, preferably less than 45 degrees, to about 90 degrees. What is needed is a device allowing greater variance in the angle at which the leg is held. Furthermore, since all positions of the knee are achieved with the upper part of the leg extending straight upward, some of these positions may leave the knee at an angle which is inconvenient for surgery. What is needed is a device allowing movement of both the upper and lower parts of the leg. Also, what is needed is a device stopping lateral movement of the knee in an adjustable manner.

U.S. Pat. No. 3,802,692 describes apparatus for controlling the attitude of a knee joint, with the apparatus including a housing secured to the center section of an operating table to support the upper part of the leg being operated on. An elongated support for the lower portion of the leg is pivotally mounted on the housing. Reversible drive means, such as a motor controlled by a foot switch pivot the support through a vertical plane to flex and extend the knee joint. Thus, with the upper leg extending horizontally, the knee joint is pivoted between a position in which the lower leg extends horizontally and a position in which the lower leg descends vertically. What is needed is a mechanism providing for extension of the knee beyond this position. Also, since this movement always occurs with the upper leg held horizontally, the knee is not necessarily located in a position convenient for the surgical procedure. Again, what is needed is a device allowing movement of both the upper and lower parts of the leg.

U.S. Pat. No. 4,091,808 describes the use of an interlocking strap to immobilize a leg for knee surgery. The strap is releasably secured around the foot and around the upper leg with the knee flexed. The strap includes an elongate portion of web material having two cooperative strips of fastening material sewn on its opposing major surfaces. The fastening material is curly pile loop and hook-type, self-gripping strip fasteners sold under the trademark VELCRO with the respective hook and loop strips mounted on respective faces of the overlapping strap portions to be fastened together around the parts of the flexed limb. As surgical procedures advance to a point where it is necessary to extend the patient's leg, the strap is removed, or the portion of the strap extending around the upper leg is released and re-fastened to provide a different degree of extension.

U.S. Pat. No. 4,209,012 describes an apparatus for maintaining a patient's knee at a predetermined degree of inflection for a desired time interval. The device includes a foot engaging means, such as a conical foot holder, which is attached to an adjustable strap to engage the patient's thigh and a means for fixing the strap length once it has been adjusted. The adjustable strap includes an inner loop which extends around the patient's thigh, and an outer loop, which is clamped together to establish the length of the inner loop, and thereby to establish the degree of inflection of the knee. This length adjustment is varied as required during a surgical operation.

While the devices of U.S. Pat. Nos. 4,091,808 and 4,209,012 provide a means for establishing and adjusting the degree of inflection of the patient's knee, a provision is not made for controlling lateral movement of the knee. The leg is free to rotate laterally at the hip, with only a distance between the ankle and the thigh where the strap is attached being held. The rotation of the leg may be accompanied by movement of the foot. What is needed is a way to prevent such rotation of the hip and movement of the foot.

U.S. Pat. Nos. 5,007,912 and 5,514,143 describe apparatus for positioning the femur and tibia of a leg during prosthetic knee surgery. Each of these devices includes a femoral section fixedly mounted on the femur and a tibial section fixedly mounted on the tibia, together with a mechanism extending between the femoral and tibial sections to control their relative movement. While precise positioning and movement of the bones are achieved in this way, these advantages are obtained at the expense or requiring elaborate mechanisms and frameworks adjacent the knee and leg. What is needed is a way for holding the knee in a variety of positions without requiring the positioning of mechanical devices immediately adjacent the knee, so that access to the knee during the surgical procedures is not impeded.

Several U.S. patents describe devices for holding the leg during arthroscopic knee surgery without addressing the question of supporting the lower leg in a manner allowing variation in the position of the knee, since the type of movement advantageously applied during prosthetic knee surgery is not needed during arthroscopic knee surgery. For example, U.S. Pat. Nos. 4,549,540 and 4,457,302 describe devices for immobilizing the patient's thigh during arthroscopic knee surgery without addressing the question of holding or supporting the lower leg. U.S. Pat. No. 4,407,277 describes apparatus for holding the leg straight and for applying various torques and axial forces to the knee.

SUMMARY OF THE INVENTION

It is therefore a first objective of the present invention to provide a mechanism for holding the knee at various angles of inflection during a surgical process;

It is a second objective thereof to hold the knee in a manner which is both rigid and readily adjustable;

It is a third objective thereof to provide a means for holding the leg to prevent lateral rotation of the leg about the hip during knee surgery;

It is a fourth objective thereof to provide for the lateral adjustment of the knee position during surgery; and It is a fifth objective thereof to provide apparatus which can be sterilized for use within the sterile field.

According to a first aspect of the present invention, there is provided apparatus for restraining a human leg during a surgical procedure. The apparatus includes an attachment platform, a leg receiving structure, and first and second attachment mechanisms. The attachment platform has an upward-facing attachment surface. The leg receiving structure, which is for holding a portion of the leg, has a downward-facing attachment surface. The first attachment mechanism is for releasably attaching the downward-facing attachment surface to the upward-facing attachment surface. The second attachment mechanism is for releasably attaching the attachment platform to the operating table.

DESCRIPTION OF THE INVENTION

Figure 1:
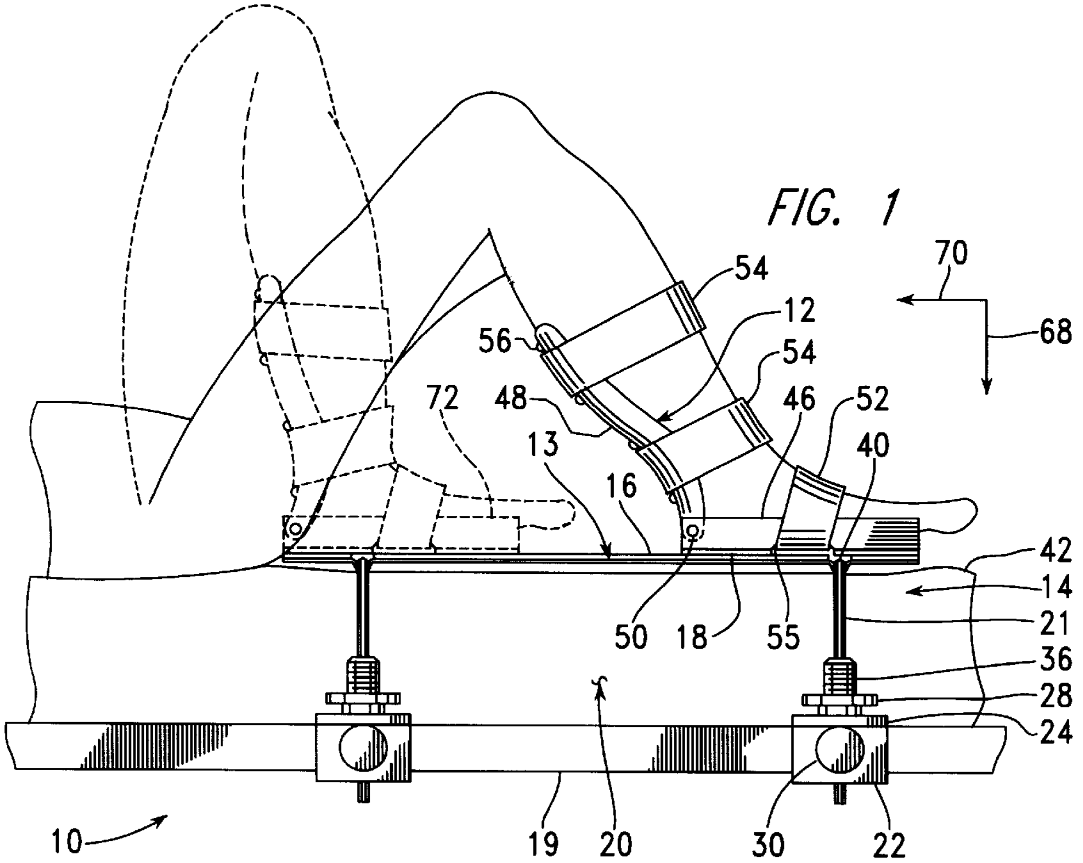
FIG. 1 is a front elevation of foot restraint apparatus built in accordance with the present.

FIG. 1 is a front elevation of the apparatus of the present invention, showing its use to hold a patient's foot in place during a knee operation. This apparatus is particularly useful during prosthetic knee replacement surgery. The apparatus consists of a support table, generally indicated as 10, and a leg receiving structure, generally indicated as 12. The support table 10 includes an attachment platform 13 and a pair of adjustable clamping arms, generally indicated as 14. A loop-type pad 16, comprised of material sold under the trademark VELCRO, extends along the upper surface of the support table 10. A hook-type pad 18, also comprised of material sold under the trademark VELCRO, extends along the lower surface of the leg receiving structure 12, allowing the foot to be placed and held in various positions along the support table 10.

Figure 2:
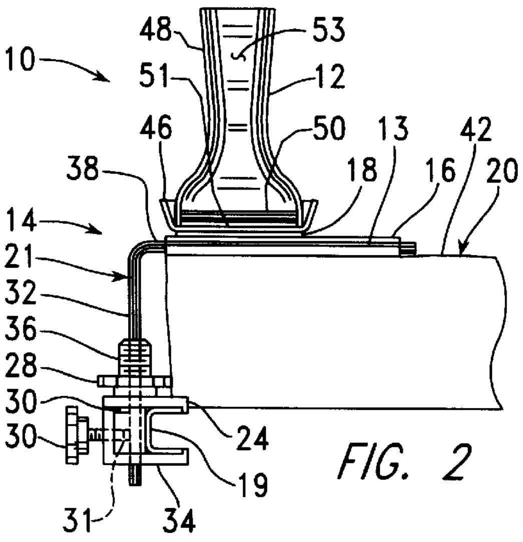
FIG. 2 is an end elevation of the foot restraint apparatus of FIG. 1.

FIG. 2 is a right end view of the apparatus of FIG. 1, showing the construction of the clamping arms 14, which removably attach the support table 10 to a rail 19 of the operating table 20. For clarity, the patient and fastening straps shown in FIG. 1 are not shown in FIG. 2.

Referring to FIGS. 1 and 2, each of the clamping arms 14 includes an "L"-shaped member 21 having a round cross-section, a sliding clamping block 22, an upper clamping jaw 24, a clamping nut 28, and a clamping screw 30. The clamping block 22 is slidably mounted on a lower leg 32 of an associated "L"-shaped member 21, being clamped into place by rotation of the clamping screw 30 within a threaded hole 32 of the clamping block 22. The clamping block 22 also includes a lower clamping jaw 34, which engages the rail 19 from below. The upper clamping jaw 24 is tightened against the rail 19 from above by turning the clamping nut 28 against the upper clamping jaw 24 and n engagement with a threaded section 36 of the clamping block 22. The upper leg 38 of the "L"-shaped member 21 extends within a transverse groove 40 of the attachment platform 13, so that when the two clamping arms 14 are clamped into place on the rail 19, the attachment platform 13 is held against the upper surface 42 of the operating table 20. The loop-type VELCRO pad 16 extending along the upper surface of the attachment platform 13 is divided into three sections at the two transverse grooves 40 so that the upper legs 28 of the "L"-shaped members 21 can be easily installed within the transverse grooves 40. The attachment platform 13 also includes three longitudinally-extending ribs 44, which are provided to increase the stiffness of the attachment platform 13. The loop-type pad 16 extends across the depressions associated with these ribs 44 within the upper surface of the attachment platform 13.

The leg receiving structure 12 includes a foot holder 46, to which the hook-type VELCRO pad 18 is attached, and a leg holder 48, which is pivotally attached to the foot holder 46 by means of a pin 50. The patient's foot is strapped within a foot receiving cavity 51 in the foot holder 46 by means of a foot strap 52, and the patient's lower leg is strapped in a leg-receiving cavity 53 of the leg holder 48 by means of a pair of leg straps 54. The foot strap 52 is held within a corresponding groove 55 in the lower surface of the foot holder 46, with the hook-type pad 18 extending as separate pieces in each direction from the groove 55. Each leg strap 54 is restrained from sliding along the leg holder 48 by means of a pair of cleats 56 extending outward as part of the leg holder 48. Each strap 52, 54 may be, for example, a tightly wrapped bandage held in place with a clamp, a fabric strap fastened to itself by means of VELCRO closures, or a leather strap fastened in place with a metal buckle.

Figure 3:
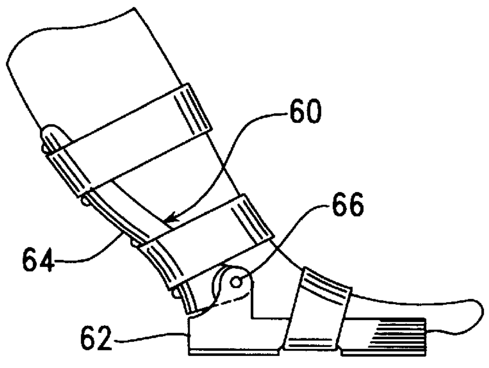
FIG. 3 is a front elevation of a leg and foot receiving structure which is an alternative to a corresponding structure in the apparatus of FIG. 1.

FIG. 3 is a front elevation of an alternate version 60 of a leg receiving structure, having a foot holder 62 and a leg holder 64 pivotally mounted to one another by means of a pair of pins 66 extending in axial alignment with one another and with the ankle of a foot placed within the foot receiving cavity 68 in the foot holder 63. The pins 66 are on opposite sides of the foot receiving cavity 68. While this alternate version 60 has the disadvantage, when compared to the leg receiving structure 12, or requiring two pins 66 instead of the single pin 50, has an advantage of more nearly duplicating the movement of the leg when the foot is flexed, so that less sliding of the straps 52, 54 occurs as the foot is flexed.

Conventional VELCRO closures are configured so that loops from the loop-type pad, such as pad 16, are forced over and onto hooks from the hook type pad, such as pad 18, as the two pads are brought together. Subsequently, the pads are relatively easily separated by pulling apart, through the application of a tension force, as the hooks are flexed to release the loops. However, a shear force applied in any direction along the plane in which the pads 16, 18 are fastened together is resisted, with the pads 16, 18 being held together, even though the shear force is much greater in magnitude than the tension force required to pull the pads 16, 18 apart. Thus, the patient's foot is positioned by pressing the foot holder 46 downward, in the direction of arrow 68, atop the attachment platform 13 and is subsequently removed by pulling the foot holder 46 upward from the attachment platform 13, being repositioned as desired during the surgical procedure.

Alternately, VELCRO closures may be configured, for example, by changing the configuration of loops within the loop-type pad, to provide for ease of release between the loop-type pad and the hook-type pad in a particular direction of shear. In the apparatus 10, this alternate type of VELCRO closures is installed so that rearward movement of the foot holder 46, in the direction of arrow 70, easily releases the attachment between the foot holder 46 and the attachment platform 13. In this alternative configuration, since the foot normally presses forward, opposite the direction of arrow 70, it is held in place until a deliberate attempt is made to move it.

Thus, as convenient or necessary during a surgical procedure, the angle at which the patient's knee is flexed is changed by releasing the attachment between the VELCRO pads 16, 18, by repositioning the patients leg as desired, and by pressing the foot holder 46 downward to reattach the VELCRO pads 16, 18. For example, the foot holder 46 may be moved between the position in which it is shown and the position indicated by dashed lines 72, with the pivotal attachment between the foot holder 46 and the leg holder 48 allowing movement of the leg holder 48 with angular movement occurring at the patient's ankle. Thus, the apparatus of the present invention is used to hold the patient's knee in various positions without a need to surround the knee itself with a framework and mechanism, so that an advantage is achieved over the use of the prior art apparatus described in U.S. Pat. Nos. 5,007,912 and 5,514,143. The attachment of the foot holder 46 to the attachment platform 13, together with the pivotal attachment of the foot holder 46 to the leg holder 48 also restrains lateral movement of the knee through rotation at the hip, thus achieving an advantage over the use of prior art apparatus described in U.S. Pat. Nos. 4,091,808 and 4,219,012.

Using the apparatus of the present invention, a knee operation is begun, for example, with the apparatus in the position shown by dashed lines 72, so that the knee is fully flexed. During the operation, the apparatus is moved one or more times in order to determine the success of the operative procedures with the knee in various states of extension.

The apparatus of the present invention is preferably sterilized during process of manufacture and packaging, and is supplied within sterile packaging to allow use of the apparatus within the sterile field of the operation.

While the present invention has been described in its preferred forms of embodiments with some degree of particularity, it is understood that this description has been given only by way of example and that numerous changes in the details of construction, fabrication, and use, including changes in the combination and arrangement of parts, may be made without departing from the spirit and scope of the invention.

I claim:

1. Apparatus for restraining a human leg during a surgical procedure, wherein said apparatus comprises:

an attachment platform having an upward-facing attachment surface;

a leg receiving structure for holding a portion of said leg, wherein said leg receiving structure has a downward-facing attachment surface, wherein said leg receiving structure includes a foot holder having an upward-facing foot cavity for holding a foot of said leg, and a first restraining belt for holding said foot within said foot cavity, wherein said downward-facing attachment surface extends along a lower surface of said foot holder, wherein said leg receiving structure additionally includes a leg holder having a leg cavity for holding a lower portion of a leg having a foot within said foot cavity and a second restraining belt for holding said lower portion of a leg within said leg cavity, and wherein said leg holder is pivotally mounted on said foot holder;

first attachment means for releasably attaching said downward-facing attachment surface to said upward-facing attachment surface in a plurality of positions along said upward-facing attachment surface; and second attachment means for releasably attaching said attachment platform to said operating table.

2. The apparatus of claim 1, wherein said leg holder is pivotally mounted on said foot holder by means of a pin extending through said foot holder at a rear end of said foot holder and through said leg holder at a lower end of said leg holder.

3. The apparatus of claim 1, wherein said leg holder is pivotally mounted on said foot holder by means of a pair of pins extending between opposite sides of said foot holder and of said leg holder in approximate alignment with an ankle of said foot within said foot cavity.

4. The apparatus of claim 1, wherein said upward-facing attachment surface and said downward-facing attachment surface comprise first and second corresponding portions of a loop-type pad and a hook-type pad, said hook-type pad engages said loop-type pad when said hook-type pad and said loop-type pad are overlapped and pressed together, said hook-type pad engaged with said loop-type pad tenaciously clings to said loop type pad upon application of a shear force to said hook-type pad, and said hook-type pad engaged with said loop-type pad releases from said loop-type pad upon application of a tensile force pulling said hook-type pad away from said loop-type pad.

5. The apparatus of claim 1, wherein said upward-facing attachment surface and said downward-facing attachment surface comprise first and second corresponding portions of a loop-type pad and a hook-type pad, said hook-type pad engages said loop-type pad when said hook-type pad and said loop-type pad are overlapped and pressed together, said hook-type pad engaged with said loop-type pad releases from said loop-type pad upon application of a shear force to said hook type pad in a first shearing direction, and said hook-type pad engaged with said loop-type pad tenaciously clings to said loop-type pad upon application of a shear force opposite said first shearing direction.

6. Apparatus for restraining a human leg during a surgical procedure, wherein said apparatus comprises:

an attachment platform having an upward-facing attachment surface;

a leg receiving structure for holding a portion of said leg, wherein said leg receiving structure has a downward-facing attachment surface;

first attachment means for releasably attaching said downward-facing attachment surface to said upward-facing attachment surface in a plurality of positions along said upward-facing attachment surface, wherein said upward-facing attachment surface and said downward-facing attachment surface comprise first and second corresponding portions of a loop-type pad and a hook-type pad, wherein said hook-type pad engages said loop-type pad when said hook-type pad and said loop-type pad are overlapped and pressed together, wherein said hook-type pad engaged with said loop-type pad tenaciously clings to said loop-type pad upon application of a shear force to said hook-type pad, and wherein said hook-type pad engaged with said loop-type pad releases from said loop-type pad upon application of a tensile force pulling said hook-type pad away from said loop-type pad; and second attachment means for releasably attaching said attachment platform to said operating table.

7. Apparatus for restraining a human leg during a surgical procedure, wherein said apparatus comprises:

an attachment platform having an upward-facing attachment surface;

a leg receiving structure for holding a portion of said leg, wherein said leg receiving structure has a downward-facing attachment surface;

first attachment means for releasably attaching said downward-facing attachment surface to said upward-facing attachment surface in a plurality of positions along said upward-facing attachment surface, wherein said upward-facing attachment surface and said downward-facing attachment surface comprise first and second corresponding portions of a loop-type pad and a hook-type pad, wherein said hook-type pad engages said loop-type pad when said hook-type pad and said loop-type pad are overlapped and pressed together, wherein said hook-type pad engaged with said loop-type pad releases from said loop-type pad upon application of a shear force to said hook-type pad in a first shearing direction, and wherein said hook-type pad engaged with said loop-type pad tenaciously clings to said loop-type pad upon application of a shear force opposite said first shearing direction; and second attachment means for releasably attaching said attachment platform to said operating table.

8. Apparatus for restraining a human leg during a surgical procedure, wherein said apparatus comprises:

an attachment platform having an upward-facing attachment surface;

a leg receiving structure for holding a portion of said leg, wherein said leg receiving structure has a downward-facing attachment surface;

first attachment means for releasably attaching said downward-facing attachment surface to said upward-facing attachment surface in a plurality of positions along said upward-facing attachment surface; and second attachment means for releasably attaching said attachment platform to said operating table, wherein said second attachment means includes an upward-facing transverse slot extending across said attachment platform, an "L"-shaped member having an upper leg extending within said first upward-facing transverse slot and a descending lower leg, and a clamping structure attached to said descending lower leg of said first "L"-shaped member, wherein said clamping structure includes a first clamping means for attachment to a rail of said operating table.

9. The apparatus of claim 8, wherein said first clamping structure includes:

a clamping block having a hole through which said descending lower leg of said first "L"-shaped member extends, and a first jaw for engaging a first side of said rail;

a set screw attaching said clamping block to said descending lower leg of said first "L"-shaped member in an adjustable manner;

a second jaw for engaging a second side of said rail opposite said first side of said rail; and a threaded member engaging said clamping block and said second jaw to hold said second jaw against said second side of said rail.

10. Apparatus for restraining a human leg during a surgical procedure, wherein said apparatus comprises:

an attachment platform having an upward-facing attachment surface;

a leg receiving structure for holding a portion of said leg, wherein said leg receiving structure has a downward-facing attachment surface;

first attachment means for releasably attaching said downward-facing attachment surface to said upward-facing attachment surface in a plurality of positions along said upward-facing attachment surface; and second attachment means for releasably attaching said attachment platform to said operating table, wherein said second attachment means includes a pair of upward-facing transverse slots extending across said attachment platform near opposite ends of said attachment platform, a pair of "L"-shaped members, wherein each "L"-shaped member has an upper leg extending within an upward-facing transverse slot within said pair of upward-facing transverse slots and a descending lower leg, and a clamping structure attached to said descending lower leg of each said "L"-shaped member, wherein each said clamping structure includes clamping means for attachment to a rail of said operating table.

11. The apparatus of claim 10, wherein said first clamping structure includes:

a clamping block having a hole through which said descending lower leg of said first "L"-shaped member extends, and a first jaw for engaging a first side of said rail;

a set screw attaching said clamping block to said descending lower leg of said first "L"-shaped member in an adjustable manner;

a second jaw for engaging a second side of said rail opposite said first side of said rail; and a threaded member engaging said clamping block and said second jaw to hold said second jaw against said second side of said rail.

* * * * *